(12) United States Patent
Yamada et al.

(10) Patent No.: US 7,348,128 B2
(45) Date of Patent: Mar. 25, 2008

(54) PHOTOSENSITIVE RESIN BASED ON SAPONIFIED POLYVINYL ACETATE PHOTOSENSITIVE RESIN COMPOSITION, METHOD OF FORMING AQUEOUS GEL FROM THE SAME, AND COMPOUND

(75) Inventors: Seigo Yamada, Ichikawa (JP);
Masahiro Takano, Inba-gun (JP);
Mitsuharu Miyazaki, Inba-gun (JP);
Shin Utsunomiya, Miyako (JP)

(73) Assignee: Toyo Gosei Co., Ltd., Ichikawa-shi, Chiba (JP)

( * ) Notice: Subject to any disclaimer, the term of this patent is extended or adjusted under 35 U.S.C. 154(b) by 320 days.

(21) Appl. No.: 10/538,690

(22) PCT Filed: Nov. 13, 2003

(86) PCT No.: PCT/JP03/14467

§ 371 (c)(1),
(2), (4) Date: Jun. 10, 2005

(87) PCT Pub. No.: WO2004/052947

PCT Pub. Date: Jun. 24, 2004

(65) Prior Publication Data

US 2006/0148925 A1 Jul. 6, 2006

(30) Foreign Application Priority Data

Dec. 10, 2002 (JP) ............................. 2002-358263

(51) Int. Cl.
*C08F 2/46* (2006.01)
*G03C 1/00* (2006.01)

(52) U.S. Cl. ................ 430/281.1; 430/269; 430/270.1; 430/286.1; 430/287.1; 430/909; 522/162; 522/178; 522/179; 522/181; 522/182; 522/113; 522/114; 522/120; 522/122; 522/104; 522/105; 528/230; 528/246; 528/248; 528/249; 528/250; 528/271; 528/272; 528/279; 528/365; 528/366; 525/55; 525/56; 525/58; 525/59; 525/62

(58) Field of Classification Search ................ 522/162, 522/178, 179, 181, 182, 113, 114, 120, 122, 522/104, 105, 121; 528/230, 246, 248, 249, 528/250, 271, 272, 297, 365, 366; 526/55, 526/56, 58, 59, 62; 430/269, 270.1, 280.1, 430/281.1, 286.1, 287.1, 909; 525/55, 56, 525/58, 59, 62

See application file for complete search history.

(56) References Cited

U.S. PATENT DOCUMENTS

2007/0109375 A1* 5/2007 Yamauchi et al. .......... 347/100

FOREIGN PATENT DOCUMENTS

EP 0 726 486 A2 8/1996

| EP | 1 216 830 A2 | 6/2002 |
| EP | 1702961 A1 * | 9/2006 |
| JP | 60-222442 | 11/1985 |
| JP | 63-075552 | 4/1988 |
| JP | 02-240555 | 9/1990 |
| JP | 08-99968 | 4/1996 |
| JP | 10003167 A * | 1/1998 |
| JP | 11-327139 | 11/1999 |
| JP | 11327139 A * | 11/1999 |
| JP | 2000-181062 | 6/2000 |
| JP | 2001-058972 | 3/2001 |

(Continued)

OTHER PUBLICATIONS

Supplementary European Search Report for European Application No. EP03772745 (foreign counterpart application) dated Jan. 19, 2007.

(Continued)

*Primary Examiner*—Sanza L. McClendon
(74) *Attorney, Agent, or Firm*—Brian A. Gomez; Gomez International Patent Office, LLC (57) ABSTRACT

A photosensitive resin which exhibits excellent storage stability, affinity, miscibility, or solubility with respect to a variety of compounds, and high sensitivity can be solidified even under hydrous conditions as well as exhibiting high cure-related sensitivity and high flexibility and being uniformly solidified even under highly hydrous conditions, a photosensitive resin composition containing the resin, and a novel compound.

The photosensitive resin is a saponified poly(vinyl acetate)-based photosensitive resin having a structural unit represented by formula (1):

(1)

$$\left[ H_2C{=}\underset{R_1}{C}{-}\underset{\underset{O}{\|}}{C}{-}O{-}R_2{-}O{-}\underset{H_2}{C}{-}\underset{OH}{CH}{-}\underset{H_2}{C}{-}X \right]_n \left\{ Y{-}CH \begin{matrix} O{-}CH \\ \phantom{O}\diagdown CH_2 \\ O{-}CH \\ \phantom{O}\diagup \\ \phantom{O}CH_2 \end{matrix} \right\}$$

(wherein $R_1$ represents H or Me; $R_2$ represents a linear or branched C2-C10 alkylene group; n is an integer of 1 to 3; X represents $$\diagdown O \diagup \ , \quad \diagdown O{-}\underset{\underset{O}{\|}}{C}{-}\underset{H_2}{C}{-}O \diagup \ , \quad \diagdown O{-}\underset{\underset{O}{\|}}{C}{-}\left(\underset{H_2}{C}\right)_m \diagup \ ;$$

m is an integer of 0 to 6; and Y represents an aromatic ring or a single bond).

10 Claims, 3 Drawing Sheets

FOREIGN PATENT DOCUMENTS

| | | | |
|---|---|---|---|
| JP | 2001058972 A | * | 3/2001 |
| JP | 2004161942 A | * | 6/2004 |
| WO | WO 96/18133 A | | 6/1996 |
| WO | PCT WO 97/33202 | | 9/1997 |
| WO | WO 2005012448 A2 | * | 2/2005 |

* cited by examiner

PHOTOSENSITIVE RESIN BASED ON SAPONIFIED POLYVINYL ACETATE PHOTOSENSITIVE RESIN COMPOSITION, METHOD OF FORMING AQUEOUS GEL FROM THE SAME, AND COMPOUND

TECHNICAL FIELD

The present invention relates to a novel poly(vinyl acetate)-based photosensitive resin and a photosensitive resin composition containing the resin, which can be used for forming a photocurable coating or a photocurable hydrogel or in pattern formation by use of an aqueous developer. The present invention also relates to novel compounds.

BACKGROUND ART

In recent years, a non-thermal method, employing a photocurable resin, for immobilizing an enzyme or bacterial cells has become known as an advantageous method in waste-water treatment and diagnosing drugs. Among such photosensitive resins, PVA-SbQ resin is employed in some applications (Japanese Patent Publication (kokoku) No. 8-23545 and Japanese Patent Application Laid-Open (kokai) No. 2-240555).

PVA-SbQ resin is applicable to a variety of uses by virtue of high stability and safety. However, since PVA-SbQ resin has a cationic moiety in the molecule, only limited quantities of these compounds can be dissolvable or miscible in immobilization of an enzyme or bacterial cells, which is problematic.

PVA-SbQ resin has another drawback. When the PVA-SbQ is in a poorly dried state and contains a large amount of water, its photosensitivity decreases considerably. Thus, when a compound that cannot be subjected to a drying step is immobilized under hydrous conditions, hardenability of the resin is insufficient.

The present inventors previously developed a photopolymerizable saponified poly(vinyl acetate)-based photosensitive resin having a specific structure as a material which exhibits excellent storage stability, affinity, miscibility, or solubility with respect to a variety of compounds. This is described in Japanese Patent Application Laid-Open (kokai) No. 2000-181062.

The photosensitive resin and the composition thereof disclosed in Japanese Patent Application Laid-Open (kokai) No. 2000-181062 are excellent as a photoresist. In this application, an aqueous solution is applied to a substrate, dried, patternwise exposed, and developed. However, the phototosensitivity of the materials is insufficient for use as a photosensitive gel-forming agent that forms gel through photocuring under water-rich conditions. Thus, a photosensitive resin and a photosensitive resin composition exhibiting higher sensitivity have been desired.

In addition to Japanese Patent Application Laid-Open (kokai) No. 2000-181062, WO97/33202 discloses some similar polymerizable photosensitive resins formed of saponified poly(vinyl acetate) having a vinylic unsaturated bond-containing fragment as a pendant group for use as a photoresist for forming a pattern. However, the above disclosed photosensitive resins also exhibit poor photosensitivity.

(Meth)acrylic acid derivatives having in the molecules thereof a moiety which is similar to a pendant molecular chain included in the saponified poly(vinyl acetate) disclosed above are reported in Japanese Patent Application Laid-Open (kokai) Nos. 2001-58972 and 11-327139. However, these documents do not disclose that the (meth)acrylic derivatives can be used in aqueous or water-containing compositions, and water-solubility of the derivatives is not confirmed in the descriptions.

SUMMARY OF THE INVENTION

The present invention provides a photosensitive resin which exhibits excellent storage stability, affinity, miscibility, or solubility with a variety of compounds, and high sensitivity. In addition, the resin can be solidified even under hydrous conditions and exhibits high cure-related sensitivity and high flexibility and can be uniformly solidified even under highly hydrous conditions. The present invention also provides a photosensitive resin composition containing the resin. The present invention further provides a compound which can be used to make these resins.

The present invention is based on the discovery that a saponified poly(vinyl acetate)-based photosensitive resin having a structural unit represented by formula (1) shown below exhibits high cure-related sensitivity and high flexibility and can be uniformly solidified even under highly hydrous conditions.

Accordingly, a first mode of the present invention provides a saponified poly(vinyl acetate)-based photosensitive resin characterized by having a structural unit represented by formula (1):

$$\left[ H_2C = \underset{R_1}{\overset{\overset{\displaystyle O}{\|}}{C}} - \overset{\displaystyle O}{C} - O - R_2 - O - \overset{H_2}{C} - \underset{OH}{\overset{\displaystyle |}{CH}} - \overset{H_2}{C} - X \right]_n Y - \text{CH} \underset{O-CH}{\overset{O-CH}{<}} \underset{CH_2}{\overset{CH_2}{|}}$$

(wherein $R_1$ represents H or Me; $R_2$ represents a linear or branched C2-C10 alkylene group; n is an integer of 1 to 3; X represents m is an integer of 0 to 6; and Y represents an aromatic ring or a single bond).

A second mode of the present invention provides a photosensitive resin composition comprising a photosensitive resin of the first mode.

A third mode of the present invention is drawn to a specific embodiment of the composition of the second mode, which further contains at least one photopolymerization initiator.

A fourth mode of the present invention is a specific embodiment of the composition of the second or third mode, which further comprise water.

A fifth mode of the present invention provides a method for forming a hydrogel comprising subjecting a photosensitive resin composition of any of the second to fourth modes to photopolymerization.

A sixth mode of the present invention provides a compound represented by formula (2):

(wherein $R_1$ represents H or Me; $R_2$ represents a linear or branched C2-C10 alkylene group; X represents m is an integer of 0 to 6; and Y represents an aromatic ring or a single bond).

A seventh mode of the present invention provides a compound represented by formula (3):

(wherein $R_1$ represents H or Me; $R_2$ represents a linear or branched C2-C10 alkylene group; X represents m is an integer of 0 to 6; Y represents an aromatic ring or a single bond; and each of $R_3$ and $R_4$ represents a C1-C3 alkyl group).

DETAILED DESCRIPTION OF THE INVENTION

The photosensitive resin of the present invention having a structural unit represented by formula (1) can be produced through acetalization of saponified poly(vinyl acetate) with a compound represented by formula (2) or (3).

Alternatively, the photosensitive resin having a structural unit represented by formula (1) can be synthesized through acetalization of saponified poly(vinyl acetate) with a carboxylic acid compound having an aldehyde group, a phenol having an aldehyde group, or an acetalized product thereof, followed by addition of hydroxyalkyl acrylate glycidyl ether to a carboxylic group or a phenolic hydroxyl group.

The saponified poly(vinyl acetate) which can be used in the present invention can vary widely. The saponified poly (vinyl acetate) preferably has a polymerization degree of 200 to 5,000. When the polymerization degree is less than 200, coating film strength is poor, whereas when the polymerization degree is in excess of 5,000, viscosity of a solution thereof excessively increases, resulting in difficulty in handling. The degree of saponification of this component is preferably 60% or more, more preferably 70% or more. When the degree of saponification is less than 60%, sufficient water solubility cannot be attained.

In order to control developability and enhance resist physical properties, the aforementioned saponified poly(vinyl acetate) can be a saponified poly(vinyl acetate) copolymer with a vinyl monomer or a modified saponified poly (vinyl acetate) such as a hydrophilic-group modified, an oleophilic-group-modified, a terminal-modified, a cationic modified, or an anionic modified saponified poly(vinyl acetate).

The compound represented by formula (2) or (3) can be produced through addition of hydroxyalkyl acrylate glycidyl ether to a carboxylic acid compound having an aldehyde group or an acetalized product thereof, or through addition of hydroxyalkyl acrylate glycidyl ether to a phenol having an aldehyde group or an acetalized product thereof. The addition reaction is similar to a known reaction disclosed, for example, in Japanese Patent Application Laid-Open (kokai) No. 60-222442.

Alternatively, these compounds can also be prepared by an addition reaction of an epoxy-group-containing aldehyde or an acetalized product thereof to hydroxyalkyl (meth) acrylate. Still another method which can be used is the transesterification between alkyl (meth)acrylate and an addition reaction product of hydroxyalkyl acrylate glycidyl ether with a carboxylic acid compound having an aldehyde group or an acetalized product thereof, or a phenol having an aldehyde group or an acetalized product thereof. However, the aforementioned approache employing hydroxyalkyl acrylate glycidyl ether is most preferred, since high quality products can be readily produced at high yield.

Generally, the reaction in the above approaches employing hydroxyalkyl acrylate glycidyl ether can be caused to proceed by heating reaction substrates and/or in the presence of a catalyst. If required, a solvent can be added to the reaction system, and a polymerization inhibitor can be added so as to suppress side reaction.

A wide variety of solvents can be used in the reaction. Examples of solvents which can be used include aliphatic hydrocarbons such as hexane, heptane, octane, nonane, and decane; aromatic hydrocarbons such as benzene, toluene, xylene, and ethylbenzene; ethers such as diethyl ether, dipropyl ether, dibutyl ether, dioxane, and tetrahydrofuran; esters such as ethyl acetate, butyl acetate, amyl acetate; halogen-containing solvents such as methylene chloride, chloroform, carbon tetrachloride, Trichlen(trademark), and Tetrachlen(trademark); alcohols such as methanol; ethanol; 2-propanol; n-butanol; sec-butanol; isobutanol; tert-butanol; ethylene glycols such as ethylene glycol, diethylene glycol, triethylene glycol, and tetraethylene glycol; glycol ethers such as ethylene glycol monomethyl ether, diethylene glycol monomethyl ether, ethylene glycol diethyl ether, and diethylene glycol dimethyl ether; glycol ether acetates such as ethylene glycol monoethyl ether acetate, diethylene glycol monoethyl ether acetate, and diethylene glycol monobutyl ether acetate; propylene glycols such as propylene glycol, dipropylene glycol, and tripropylene glycol; propylene glycol ethers such as propylene glycol monomethyl ether, propylene glycol monoethyl ether, dipropylene glycol monomethyl ether, dipropylene glycol monoethyl ether, propylene glycol dimethyl ether, dipropylene glycol dimethyl ether, propylene glycol diethyl ether, and dipropylene glycol diethyl ether; propylene glycol ether acetates such as propylene glycol monomethyl ether acetate, propylene glycol monoethyl ether acetate, dipropylene glycol monomethyl ether acetate, and dipropylene glycol monoethyl ether acetate; sulfur-containing solvents such as dimethylsulfoxide and sulforane; amides such as N-methylpyrrolidone; dimethylformaide; dimethylacetamide; and mixtures thereof.

The catalyst used in the reaction can similarly vary widely. Examples of acid catalysts which can be used include inorganic acids such as sulfuric acid, phosphoric acid, perchloric acid; Lewis acids such as BF$_3$; and organic sulfonic acids such as methanesulfonic acid, benzenesulfonic acid, p-toluenesulfonic acid, and dodecylbenzenesulfonic acid. Examples of basic catalysts include tertiary amines such as triethylamine, tetramethylethylenediamine, tributylamine, tri-n-octylamine, dimethylbenzylamine, pyridine, and N,N-dimethyl-4-aminopyridine; quaternary ammonium salts such as tetramethylammonium chloride, tetramethylammonium bromide, tetraethylammonium bromide, and tetrabutylammonium bromide; and phosphorus compounds such as triphenylphosphine and tributylphosphine. Catalysts in liquid form such as pyridine and triethylamine can also be used as a solvent.

The type of polymerization inhibitor used in the present invention is not critical. Examples of inhibitors which can be used include phenol, alkylphenol, catechol, alkylcatechol, hydroquinone, hydroquinone monomethyl ether, N-alkyl-N-nitrosoaniline, N-nitroso-phenylhydroxylamine salt, phenothiazine, 2,2,6,6-tetramethylpiperidine-1-oxyl, 2,2,6,6-tetramethyl-4-hydroxypiperidine-1-oxyl, and p-methoxyphenol. Of these, 2,2,6,6-tetramethyl-4-hydroxypiperidine-1-oxyl is most preferred, since the compound satisfies the need for water-solubility required during acetalization of saponified poly(vinyl acetate).

After completion of the reaction, the solvent, catalyst, and polymerization inhibitor can be removed from the reaction system, if required. Alternatively, these species as such can be employed in reaction for acetalizing of saponified poly(vinyl acetate) without removal.

In the course of the aforementioned syntheses, in some cases, a compound represented by formula (4) or (5) is formed in a small amount as a by-product. The formed compound can be removed to purify the product of interest. However, since the presence of the formed compound is not detrimental to use of the product of interest in practice, the reaction product can be employed without subjecting it to further treatment.

(4)

(wherein symbols are the same as defined in formula (2))

(5)

(wherein symbols are the same as defined in formula (3))

The aldehyde compound represented by formula (2) and the acetal compound represented by formula (3) can be applicable to a variety of other uses.

The acetalization of saponified poly(vinyl acetate) with a compound represented by (2) or (3), thereby forming the photosensitive resin having a structural unit represented by formula (1), is generally carried out in a solution with heating and/or in the presence of a catalyst. Upon reaction, a polymerization inhibitor may be added so as to suppress side reaction. A wide variety of solvents can be used forming the solution. The solvent preferably is capable of dissolving the saponified poly(vinyl acetate). Examples of solvents which can be used include water; ethylene glycols such as ethylene glycol, diethylene glycol, triethylene glycol, and tetraethylene glycol; glycol ethers such as ethylene glycol monomethyl ether, diethylene glycol monomethyl ether, ethylene glycol diethyl ether, and diethylene glycol dimethyl ether; glycol ether acetates such as ethylene glycol monoethyl ether acetate, diethylene glycol monoethyl ether acetate, and diethylene glycol monobutyl ether acetate; propylene glycols such as propylene glycol, dipropylene glycol, and tripropylene glycol; propylene glycol ethers such as propylene glycol monomethyl ether, propylene glycol monoethyl ether, dipropylene glycol monomethyl ether, dipropylene glycol monoethyl ether, propylene glycol dimethyl ether, dipropylene glycol dimethyl ether, propylene glycol diethyl ether, and dipropylene glycol diethyl ether; propylene glycol ether acetates such as propylene glycol monomethyl ether acetate, propylene glycol monoethyl ether acetate, dipropylene glycol monomethyl ether acetate, and dipropylene glycol monoethyl ether acetate; dimethylsulfoxide; N-methylpyrrolidone; dimethylformamide; dimethylacetamide; mixtures thereof; and 2-propanol. Of these, water is preferred from the viewpoint of safety. In the case in which high-boiling point is required for an operational reason, propylene glycol, dipropylene glycol, or N-methylpyrrolidone is preferably used singly or in combination with water.

A wide variety of acid catalystscan be used in the reaction. Examples of acid catalysts include inorganic acids such as sulfuric acid, phosphoric acid, nitric acid, and perchloric acid; organic carboxylic acids such as formic acid, acetic acid, propionic acid, oxalic acid, malonic acid, succinic acid, maleic acid, fumaric acid, and phthalic acid; and organic sulfonic acids such as methanesulfonic acid, benzenesulfonic acid, p-toluenesulfonic acid, and dodecylbenzenesulfonic acid.

After completion of the reaction, preferably, these acids are neutralized with an alkaline compound such as sodium hydroxide, potassium hydroxide, ammonia, or an organic amine or with a solution thereof, or are removed by use of a basic ion-exchange resin.

The reaction temperature used depends on the type of the compound forming a pendant group and on the type and concentration of the acid catalyst. Generally, the reaction temperature is preferably from room temperature to 100° C.

During acetalization of saponified poly(vinyl acetate) with a compound represented by (2) or (3), there may be simultaneously reacted formaldehyde, acetaldehyde, propionaldehyde, butylaldehyde, benzaldehyde, hydroxybenzaldehyde, o-benzaldehydesulfonic acid a salt thereof, benzaldehyde-2,4-disulfonic acid or a salt thereof, or an acetalized product thereof.

The ratio of the compound represented by (2) or (3) to the saponified poly(vinyl acetate) into which the compound is incorporated, which varies in accordance with the type of the compound, is preferably 0.02 to 20 mol % with respect to the vinyl acetate units, more preferably 0.1 to 5 mol %. When the ratio is excessively high, developability decreases, whereas when the ratio is excessively low, sensitivity and coating film strength decrease, and formation of hydrogel becomes difficult.

The photosensitive resin of the present invention having a structural unit represented by formula (1) can be incorporated into a photosensitive resin composition. When a photosensitive resin composition is produced from the photosensitive resin of the present invention, a photopolymerization initiator or a photosensitizer is preferably added to the composition so as to promote photocrosslinking reaction. Upon incorporation of the these compounds into the composition, the compounds may be dissolved or dispersed in a solvent. Alternatively, the compounds may be chemically linked to the photosensitive resin. When the photopolymerization initiator is dissolved or dispersed in the composition, the photopolymerization initiator is generally incorporated in an amount of 0.1 to 30 wt. % with respect to the amount of the photosensitive resin, preferably 1 to 10 wt. %. A wide variety of photopolymerization initiators and photosensitizers can be used in the instantcompositions. Examples include benzophenones such as benzophenone, hydroxybenzophenone, bis-N,N-dimethylaminobenzophenone, bis-N,N-diethylaminobenzophenone, and 4-methoxy-4'-dimethylaminobenzophenone; thioxanthones such as thioxanthone, 2,4-diethylthioxanthone, isopropylthioxanthone, chlorothioxanthone, and isopropoxychlorothioxanthone; anthraquinones such as ethylanthraquinone, benzanthraquinone, aminoanthraquinone, and chloroanthraquinone; acetophenones; benzoin ethers such as benzoin methyl ether, benzoin ethyl ether, and benzoin phenyl ether; 2,4,6-trihalomethyltriazines; 1-hydroxycyclohexyl phenyl ketone; 2,4,5-triarylimidazole dimers such as 2-(o-chlorophenyl)-4,5-diphenylimidazole dimer, 2-(o-chlorophenyl)-4,5-di(m-methoxyphenyl) imidazole dimer, 2-(o-fluorophenyl)-4,5-diphenylimidazole dimer, 2-(o-methoxyphenyl)-4,5-diphenylimidazole dimer, 2-(p-methoxyphenyl)-4,5-diphenylimidazole dimer, 2,4-di (p-methoxyphenyl)-5-phenylimidazole dimer, and 2-(2,4-dimethoxyphenyl)-4,5-diphenylimidazole dimer; benzyl dimethyl ketal; 2-benzyl-2-dimethylamino-1-(4-morpholinophenyl)-butan-1-one; 2-methyl-1-[4-(methylthio)phenyl]-2-morpholino-1-propanone; 2-hydroxy-2-methyl-1-phenyl-propan-1-one; 1-[4-(2-hydroxyethoxy)-phenyl]-2-hydroxy-2-methyl-1-propan-1-one; phenanthrenequinone; 9,10-phenanthrenequinone; benzoins such as methylbenzoin and ethylbenzoin; acridine derivatives such as 9-phenylacridine and 1,7-bis(9,9'-acridinyl)heptane; bisacylphosphine oxide; and mixtures thereof.

In addition to the above initiators, other additives such as one or more promoters can also be added. Examples of promoters which can be used include ethyl p-dimethylaminobenzoate, isoamyl p-dimethylaminobenzoate, ethanolamine, diethanolamine, and triethanolamine.

To the photosensitive resin composition of the present invention, a polymerizable monomer can be added in order to regulate sensitivity of the composition and to enhance contrast and physical properties of the hardened products. Examples of such monomers include polyethylene glycol diacylate (No. of ethylene oxide unit: 2 to 14), polyethylene glycol dimethacrylate (No. of ethylene oxide unit: 2 to 14), trimethylolpropane diacrylate, trimethylolpropane dimethacrylate, trimethylolpropane triacrylate, trimethylolpropane trimethacrylate, trimethylolpropane ethoxytriacrylate, trimethylolpropane ethoxytrimethacrylate, trimethylolpropane propoxytriacrylate, trimethylolpropane propoxytrimethacrylate, tetramethylolmethane triacrylate, tetramethylolmethane trimethacrylate, tetramethylolmethane tetraacrylate, tetramethylolmethane tetramethacrylate, polypropylene glycol diacrylate (No. of propylene oxide unit: 2 to 14), polypropylene glycol dimethacrylate (No. of propylene oxide unit: 2 to 14), dipentaerythritol pentaacrylate, dipentaerythritol pentamethacrylate, dipentaerythritol hexaacrylate, dipentaerythritol hexamethacrylate, bisphenol A polyoxyethylene diacrylate, bisphenol A polyoxyethylene dimethacrylate, bisphenol A dioxyethylene diacrylate, bisphenol A dioxyethylene dimethacrylate, bisphenol A trioxyethylene diacrylate, bisphenol A trioxyethylene dimethacrylate, bisphenol A decaoxyethylene diacrylate, bisphenol A decaoxyethylene dimethacrylate, esterified products of polyhydric carboxylic acid (e.g., phthalic anhydride) and a compound having a hydroxyl group and an ethylenic unsaturated group (e.g., β-hydroxyethyl acrylate and β-hydroxyethyl methacrylate), and acrylic acid or methacrylic acid alkyl esters (e.g., methyl acrylate, methyl methacrylate, ethyl acrylate, ethyl methacrylate, butyl acrylate, butyl methacrylate, 2-ethylhexyl acrylate, and 2-ethylhexyl methacrylate).

If required, one or more conventionally known other components such as polymerization inhibitors, plasticizers, pigments, dyes, defoaming agents, and coupling agents can also be incorporated into the compositions of the invention.

The photosensitive resin composition of the present invention preferably contains water as a solvent. When the photosensitive resin composition of the present invention is produced from a photosensitive resin that has been synthesized with a solvent other than water, the synthesized photosensitive resin can be simply diluted with water. Alternatively, the synthesis solvent can be distilled off and another solvent substituted; drying to solid and dissolving the solid in water; or pouring the resin into a non-polar solvent such as aliphatic hydrocarbon, aromatic hydrocarbon, ethyl acetate, or butyl acetate; separating the precipitated solid, and re-dissolving the solid in water.

The photosensitive resin compositions of the present invention exhibit high sensitivity, even when the composition has a low concentration. Thus, when a low-concentration (e.g., about 0.5 to 50%, preferably 1% or more in solid content) aqueous solution of the composition is subjected to photopolymerization, a hydrogel can be formed.

Into the photosensitive resin composition of the present invention, any of the functional components including a variety of drug ingredients, enzymes, bacterial cells, etc. can be incorporated. In this case, a photosensitive resin composition containing any of a variety of drug ingredients, enzymes, bacterial cells, etc. is photocured, whereby a hydrogel containing any of a variety of drug ingredients, enzymes, bacterial cells, etc. can be formed. After formation of a hydrogel from the photosensitive resin composition of the present invention, the hydrogel can be impregnated with any of a variety of drug ingredients, enzymes, or bacterial cells, as will be evident to those skilled in the art.

Similar to a conventional resist composition, the photosensitive resin composition of the present invention can be patterned. Thus, a photosensitive resin composition containing any of the functional components including a variety of drug ingredients, enzymes, bacterial cells, etc. or a hydrogel formed from the photosensitive resin composition of the present invention and impregnated with any of the functional components including a variety of drug ingredients, enzymes, bacterial cells, etc. can be patterned through photolithography. The photosensitive resin composition of the present invention can be used as a conventional photoresist.

When the photosensitive resin composition of the present invention is subjected to photo-patterning, any development technique such as a spray method, a paddle method, or an immersion method can be used. Among these, the spray method is preferred, since the method produces few amounts of residues. If required, ultrasonication or other irradiation can be used.

The developer is preferably water (i.e., neutral pH conditions). Other solvents which can be use includes a weak acidic or alkaline solvent. In order to enhance developability, one or more organic solvent, surfactant, defoaming agent, etc, can also be added to the developer.

The present invention provides photosensitive resins which exhibit excellent storage stability, affinity, miscibility, or solubility with respect to a variety of compounds, and high sensitivity. These resins solidify even under hydrous conditions and exhibit high cure-related sensitivity and high flexibility. When the photosensitive resin or the photosensitive resin composition of the present invention is applied to solidification of an aqueous solution, uniform gel having high strength can be formed, even the resin or the composition is used at low concentration. When applied to photo-patterning, the resin or the resin composition serves as a novel, useful water-soluble resist exhibiting high sensitivity and attaining high resolution.

The present invention will next be described in detail by way of examples, which should not be construed as limiting the invention. A variety of photosensitive resin compositions obtained from the photosensitive resin and finding various uses fall within the scope of the present invention.

EXAMPLE 1

Terephthalaldehyde acid (60 g), 4-hydroxybutyl acrylate glycidyl ether (4HBAGE, product of Nippon Kasei Chemical Co., Ltd.) (45 g), p-methoxyphenol (0.2 g) polymerization initiator, and N,N-dimethyl-4-aminopyridine (1.4 g) catalyst were placed in a reactor, and the mixture was stirred on a hot-water bath (85° C.) for nine hours, to thereby form a reddish-brown viscous solution. Reactivity of 4-hydroxybutyl acrylate glycidyl ether was found to be 92%.

To the resulting solution (100 g), a 5 wt. % aqueous sodium carbonate solution (100 g) was added, followed by stirring the mixture for one hour. The mixture was extracted with toluene (250 g) serving as an extraction solvent, and the toluene layer was concentrated by means of an evaporator, to thereby produce a reddish-brown viscous liquid (A).

The resulting reddish-brown viscous liquid (A) was analyzed through high-performance liquid chromatography, $^1$H-NMR, and IR. High-performance liquid chromatography was performed under the following conditions: column; SUPERIOREX ODS (size 4.6 mmφ×250 mm, product of Shiseido Co., Ltd.), eluent; $CH_3CN$-0.1 wt. % aqueous phosphoric acid (40:60 vol. %), flow rate; 1.0 mL/min, column temperature; 35.0° C., detector; MD-910 (product of JASCO Corporation), and detection wavelength; 203 nm. $^1$H-NMR of a sample dissolved in TMS-containing $CDCl_3$ was measured by means of JNM-AL400 (product of JEOL Ltd.). IR was measured by means of FT/IR-410 (product of JASCO Corporation), using KBr pellet method.

Figure 1:
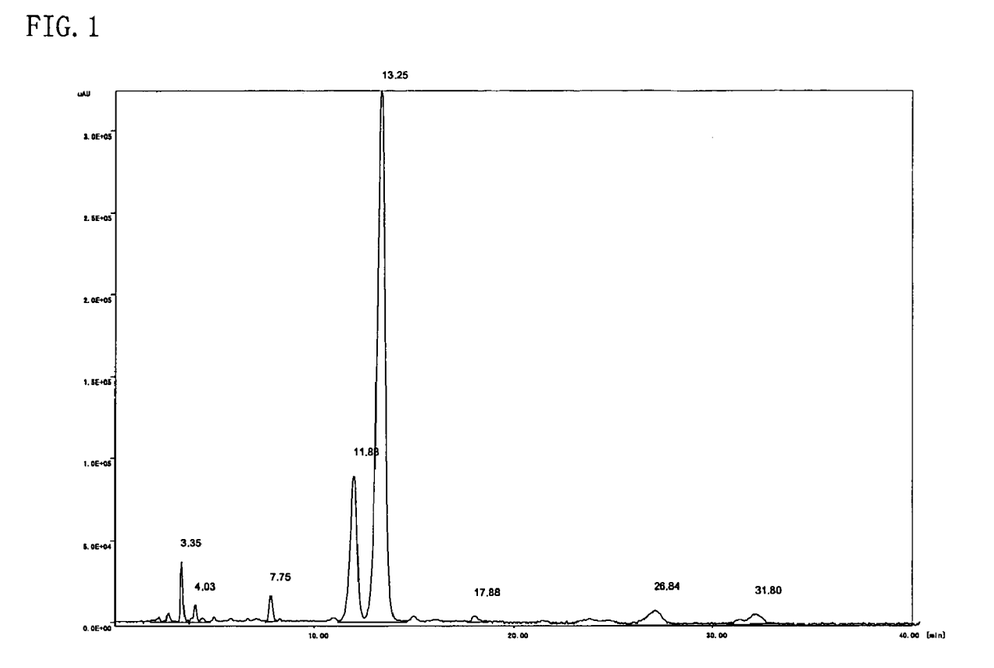
FIG. 1 is a chart showing analytical results obtained through high-performance liquid chromatography in Example 1.
Figure 2:
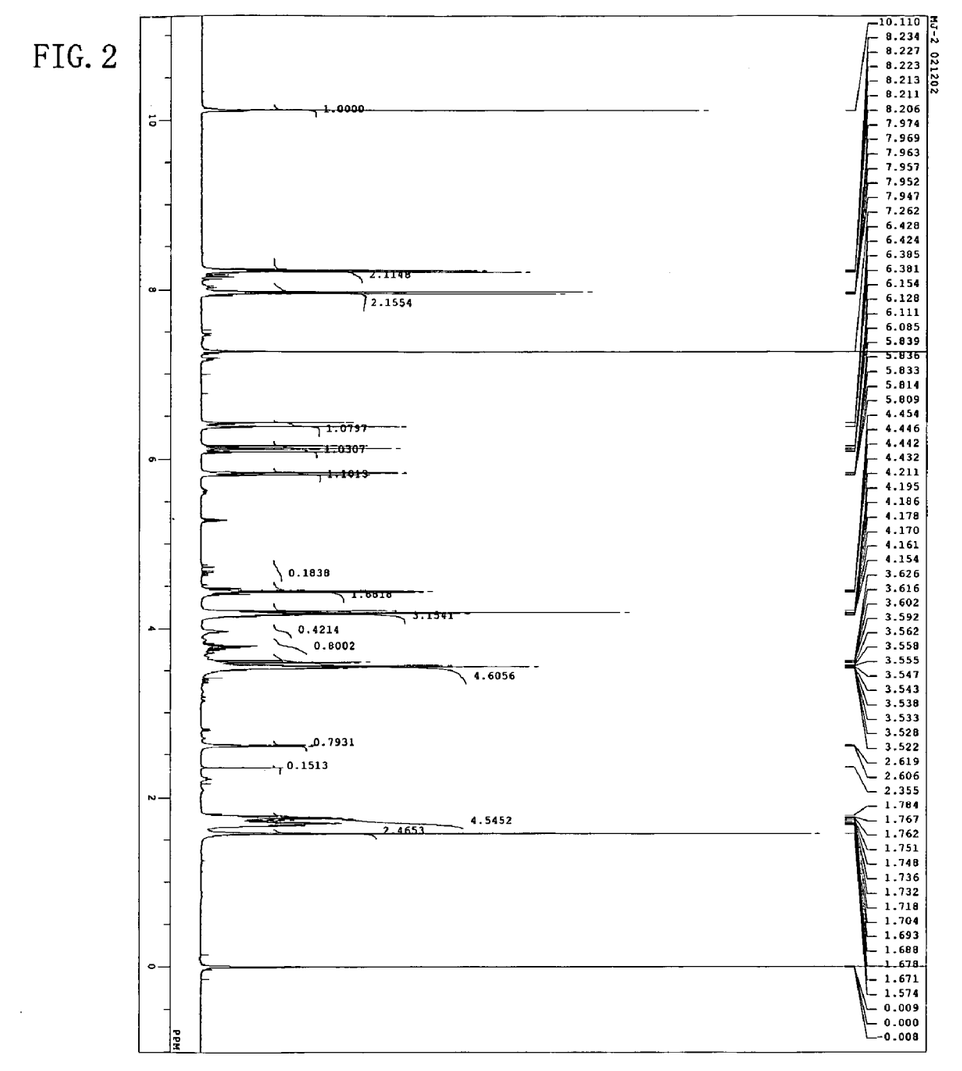
FIG. 2 is a chart showing $^1$H-NMR measurement results obtained in Example 1.
Figure 3:
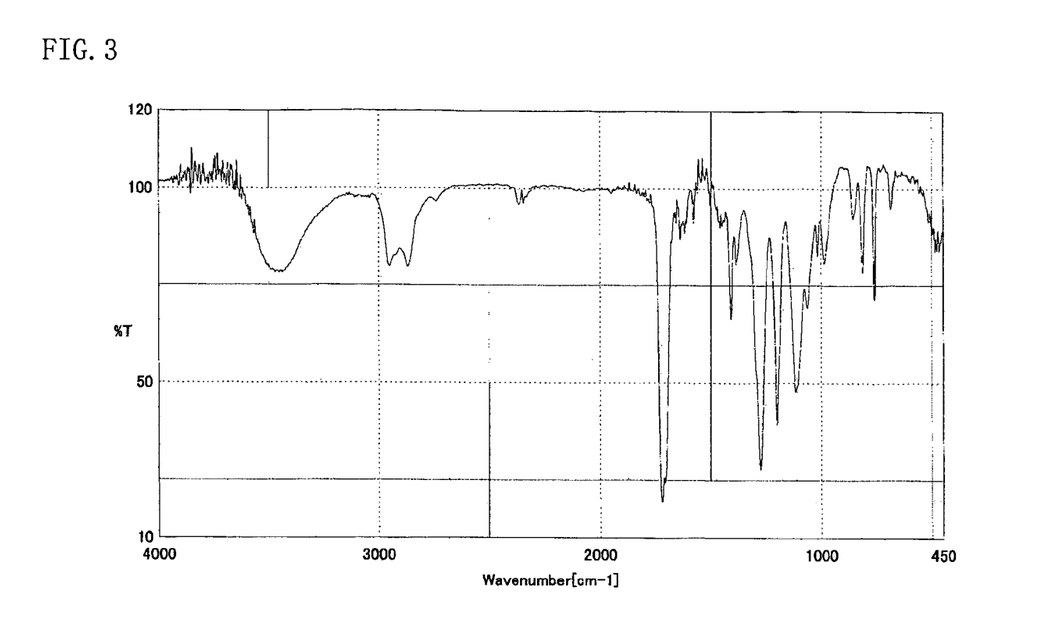
FIG. 3 is a chart showing IR measurement results obtained in Example 1.

FIG. 1 is a chart showing analytical results of the viscous liquid obtained through high-performance liquid chromatography. FIG. 2 is a chart showing $^1$H-NMR measurement results of the viscous liquid. FIG. 3 is a chart showing an IR measurement results of the viscous liquid. As is clear from the Figures, the solution was found to contain compound (B), which is a compound represented by formula (2), and an isomer that is thought to be compound (C), which is a compound represented by formula (4). The ratio of compound (B)/compound (C) was estimated to be 80/20.

EXAMPLE 2

Saponified poly(vinyl acetate) (polymerization degree; 1,700, saponification degree; 88%) (EG-30, product of Nippon Synthetic Chemical Industry Co. Ltd.) (50 g) was dispersed in purified water (430 g), and the dispersion was heated to 90° C., to thereby dissolve the polymer. The solution was cooled to 60° C. To the cooled solution, phosphoric acid (3.0 g) serving as a catalyst, the reddish-brown viscous liquid (A) (4.2 g) obtained in Example 1, 2-propanol (59 g) serving as a solvent, and 2,2,6,6-tetramethyl-4-hydroxypiperidine-1-oxyl (ADK Stab LA-7RD, product of Asahi Denka Kogyo K.K.) (13.6 mg) serving as a polymerization inhibitor were added, and the mixture was stirred at 60° C. for seven hours, to thereby produce a viscous solution. After cooling the solution to 45° C., a basic ion-exchange resin (Diaion WA20, product of Mitsubishi Chemical Corporation) (44 g) was added to the solution, and the mixture was stirred for two hours. After confirmation of neutral pH conditions of the mixture, the mixture was cooled to room temperature, and the ion-exchange resin was removed through filtration by use of a 400-mesh gauze, to thereby produce a viscous resin solution.

To the resulting solution, 1-[4-(2-hydroxyethoxy)-phenyl]-2-hydroxy-2-methyl-1-propan-1-one (Irgacure 2959, product of Ciba Specialty Chemicals K.K.) serving as a photopolymerization initiator was added in an amount of 3 wt. % with respect to the resin content of the solution, to thereby produce a photosensitive resin composition.

The resulting aqueous photosensitive resin composition solution was diluted with water, to thereby prepare samples having solid contents shown in Table 1. Each sample was placed in a test tube sealed with a stopper. The sample was irradiated with a UV ray having an illuminance of 380 mW/cm$^2$ emitted from a metal halide lamp UV radiator for 2.8 seconds. After completion of irradiation, the test tube was placed upright, and the stopper was removed. An iron ball (5.5 g) was placed on the surface of each sample, and hardenability of the samples was evaluated with comparison on the basis of the status (sinking or floating) of the iron ball. Table 1 shows the results.

TABLE 1

| Solid content | 1% | 2% | 4% | 6% | 8% | 10% |
|---|---|---|---|---|---|---|
| Iron ball | sink | Float | float | float | float | float |

EXAMPLE 3

Saponified poly(vinyl acetate) (polymerization degree; 3,000, saponification degree; 88%) (OSK-9101, product of Nippon Synthetic Chemical Industry Co. Ltd.) (37 g) was dispersed in purified water (464 g), and the dispersion was heated to 90° C., to thereby dissolve the polymer. The solution was cooled to 60° C. To the cooled solution, phosphoric acid (3.5 g) serving as a catalyst, the reddish-brown viscous liquid (A) (2.9 g) obtained in Example 1, 2-propanol (116 g) serving as a solvent, and 2,2,6,6-tetramethyl-4-hydroxypiperidine-1-oxyl (ADK Stab LA-7RD, product of Asahi Denka Kogyo K.K.) (15.6 mg) serving as a polymerization inhibitor were added, and the mixture was stirred at 60° C. for seven hours, to thereby produce a viscous solution. After cooling the solution to 45° C., a basic ion-exchange resin (Diaion WA20, product of Mitsubishi Chemical Corporation) (50 g) was added to the solution, and the mixture was stirred for two hours. After confirmation of neutral pH conditions of the mixture, the mixture was returned to room temperature, and the ion-exchange resin was removed through filtration by use of a 400-mesh gauze, to thereby-produce a viscous resin solution.

To the resulting solution, 1-[4-(2-hydroxyethoxy)-phenyl]-2-hydroxy-2-methyl-1-propan-1-one (Irgacure 2959, product of Ciba Specialty Chemicals K.K.) serving as a photopolymerization initiator was added in an amount of 3 wt. % with respect to the resin content of the solution, to thereby produce a photosensitive resin composition.

The resulting aqueous photosensitive resin composition solution was diluted with water, to thereby prepare samples having solid contents shown in Table 2. Under the same conditions as employed in Example 2, hardenability of the samples was evaluated with comparison on the basis of the status (sinking or floating) of the iron ball. Table 2 shows the results.

TABLE 2

| Solid content | 1% | 2% | 4% | 6% | 8% | 10% |
|---|---|---|---|---|---|---|
| Iron ball | float | Float | float | float | float | float |

COMPARATIVE EXAMPLE 1

PVA-SbQ resin (SPP-H-13, product of Toyo Gosei Co., Ltd., polymerization degree of 1,700) was diluted with water, to thereby prepare samples having solid contents shown in Table 3. In a manner similar to that of Example 2, hardenability of the samples was evaluated. Table 3 shows the results.

TABLE 3

| Solid content | 1% | 2% | 4% | 6% | 8% | 10% |
|---|---|---|---|---|---|---|
| Iron ball | sink | sink | sink | sink | float | float |

Tables 1 to 3 confirm that low-concentration aqueous solution samples of Example 2 (solid content: 2%) and Example 3 (solid content: 1%) formed uniform hydrogels having high gel strength and were able to maintain an iron ball on the gel surface. In contrast, the samples of Comparative Example 1 were able to maintain an iron ball on the sample surface, only when the solid content of the aqueous solution sample increased to 8%, which is a threshold concentration higher than that determined in the Examples.

EXAMPLE 4

Saponified poly(vinyl acetate) (polymerization degree; 1,700, saponification degree; 88%) (EG-30, product of Nippon Synthetic Chemical Industry Co. Ltd.) (50 g) was dispersed in purified water (354 g), and the dispersion was heated to 90° C., to thereby dissolve the polymer. The solution was cooled to 60° C. To the cooled solution, phosphoric acid (3.2 g) serving as a catalyst, the reddish-brown viscous liquid (A) (6.2 g) obtained in Example 1, 2-propanol (152 g) serving as a solvent, and 2,2,6,6-tetramethyl-4-hydroxypiperidine-1-oxyl (ADK Stab LA-7RD, product of Asahi Denka Kogyo K.K.) (14.1 mg) serving as a polymerization inhibitor were added, and the mixture was stirred at 60° C. for seven hours, to thereby produce a viscous solution. After cooling the solution to 45° C., a basic ion-exchange resin (Diaion WA20, product of Mitsubishi Chemical Corporation) (47 g) was added to the solution, and the mixture was stirred for two hours. After confirmation of neutral pH conditions of the mixture, the ion-exchange resin was removed through filtration by use of a 400-mesh gauze, to thereby produce a transparent viscous resin solution.

To the resulting solution, 1-[4-(2-hydroxyethoxy)-phenyl]-2-hydroxy-2-methyl-1-propan-1-one (Irgacure 2959, product of Ciba Specialty Chemicals K.K.) serving as a photopolymerization initiator was added in an amount of 3 wt. % with respect to the resin content of the solution, to thereby produce a photosensitive resin composition.

The resulting photosensitive resin composition was applied to the entire surface of a glass substrate by use of a blade coater, and the coated substrate was dried in a clean oven at 80° C. for five minutes, followed by cooling to room temperature. The resin composition was irradiated, using a mask having a predetermined pattern, with a UV ray by means of an ultra-high-pressure mercury lamp (illuminance: 4.0 mW/cm$^2$) at 500 mJ/cm$^2$. The thus-irradiated resin composition was developed with ion-exchanged water for 30 seconds through the spray method, to thereby form a pattern of interest. The formed pattern had a thickness of 1.0 μm and resolution of 10 μm, and the photosensitivity of the resin composition on the basis of UGRA step tablet was determined to be 5.

We claim:

1. A saponified poly(vinyl acetate)-based photosensitive resin characterized by having a structural unit represented by formula (1):

(1)

(wherein $R_1$ represents H or Me; $R_2$ represents a linear or branched C2-C10 alkylene group; n is an integer of 1 to 3; X represents m is an integer of 0 to 6; and Y represents an aromatic ring or a single bond).

2. A photosensitive resin composition comprising a photosensitive resin according to claim 1.

3. A photosensitive resin composition according to claim 2, which further comprises a least one photopolymerization initiator.

4. A photosensitive resin composition according to claim 2, which further comprises water.

5. A method for forming a hydrogel comprising subjecting a photosensitive resin composition as recited in claim 2 to photopolymerization.

6. A compound represented by formula (2):

(2)

(wherein $R_1$ represents H or Me; $R_2$ represents a linear or branched C2-C10 alkylene group; X represents m is an integer of 0 to 6; and Y represents an aromatic ring or a single bond).

7. A compound represented by formula (3):

(3)

(wherein $R_1$ represents H or Me; $R_2$ represents a linear or branched C2-C10 alkylene group; X represents m is an integer of 0 to 6; Y represents an aromatic ring or a single bond; and each of $R_3$ and $R_4$ represents a C1-C3 alkyl group).

8. A photosensitive resin composition according to claim 3, which further comprises water.

9. A method for forming a hydrogel comprising subjecting a photosensitive resin composition as recited in claim 3 to photopolymerization.

10. A method for forming a hydrogel comprising subjecting a photosensitive resin composition as recited in claim 4 to photopolymerization.

* * * * *